(12) United States Patent
Van Der Heide et al.

(10) Patent No.: US 9,884,798 B2
(45) Date of Patent: Feb. 6, 2018

(54) PROCESS FOR THE CONVERSION OF SACCHARIDE-CONTAINING FEEDSTOCK

(71) Applicant: SHELL OIL COMPANY, Houston, TX (US)

(72) Inventors: Evert Van Der Heide, Amsterdam (NL); Pieter Huizenga, Amsterdam (NL)

(*) Notice: Subject to any disclaimer, the term of this patent is extended or adjusted under 35 U.S.C. 154(b) by 0 days.

(21) Appl. No.: 14/781,735

(22) PCT Filed: Apr. 1, 2014

(86) PCT No.: PCT/EP2014/056536
§ 371 (c)(1),
(2) Date: Oct. 1, 2015

(87) PCT Pub. No.: WO2014/161859
PCT Pub. Date: Oct. 9, 2014

(65) Prior Publication Data
US 2016/0052843 A1    Feb. 25, 2016

(30) Foreign Application Priority Data
Apr. 5, 2013  (EP) .................... 13162502

(51) Int. Cl.
    *C07C 29/00*    (2006.01)
    *C07C 29/132*   (2006.01)
    *C07C 29/60*    (2006.01)
(52) U.S. Cl.
    CPC ......... *C07C 29/00* (2013.01); *C07C 29/132* (2013.01); *C07C 29/60* (2013.01)
(58) Field of Classification Search
    CPC ....... C07C 29/00; C07C 29/132; C07C 29/60; C07C 31/202; C07C 31/205
    USPC ................. 568/903; 536/56, 123.1
    See application file for complete search history.

(56) References Cited

U.S. PATENT DOCUMENTS

| | | | |
|---|---|---|---|
| 5,648,579 A * | 7/1997 | Kulprathipanja | C07C 2/66 585/446 |
| 2011/0160482 A1 | 6/2011 | Nagaki et al. | |
| 2011/0313208 A1 | 12/2011 | Kalnes et al. | |
| 2011/0313212 A1 | 12/2011 | Kalnes et al. | |
| 2012/0172633 A1 | 7/2012 | Zhang et al. | |

FOREIGN PATENT DOCUMENTS

| | | |
|---|---|---|
| CN | 102190562 | 9/2011 |
| CN | 102286548 | 12/2011 |
| CN | 102643165 | 8/2012 |
| CN | 102675045 | 9/2012 |
| WO | 2013015955 | 1/2013 |

OTHER PUBLICATIONS

International Search Report dated May 13, 2014 of PCT/EP2014/056536 filed Apr. 1, 2014.
Zhang, Ji, et al.: Direct Catalytic Conversion of Cellulose into Ehtylene Glycol Using Nickel-Promoted Tungsten Carbide Catalysts, Biomass Conversion, Angew. Chemie. Int. Ed. 2008, 47, pp. 8510-8513.
Liu, Yue, et al.: Tungsten Trioxide Promoted Selective Conversion of Cellulose into Propylene Glycol and Ethylene Glycol on a Ruthenium Catalyst, Renewable Resources, Angew. Chemie. Int. Ed. 2012, 51, pp. 3249-3253.
Liu, X. et al. "Kinetics and mechanism of thermal decomposition of corn starches with different amylose/amylopectin ratios" Starch/Starke 2010, 62, pp. 139-146.

* cited by examiner

*Primary Examiner* — Yih-Horng Shiao

(57) ABSTRACT

The invention provides a process for the catalytic conversion of a saccharide-containing feedstock in a reactor, wherein saccharide-containing feedstock is provided to the reactor as a feed stream through a feed pipe and is contacted with a catalyst system in the reactor and a reaction product is continuously removed from the reactor and wherein the saccharide-containing feedstock is provided through the feed pipe as a pulsed flow and is alternated with a second feed stream comprising a solvent being provided through the same feed pipe.

11 Claims, 1 Drawing Sheet

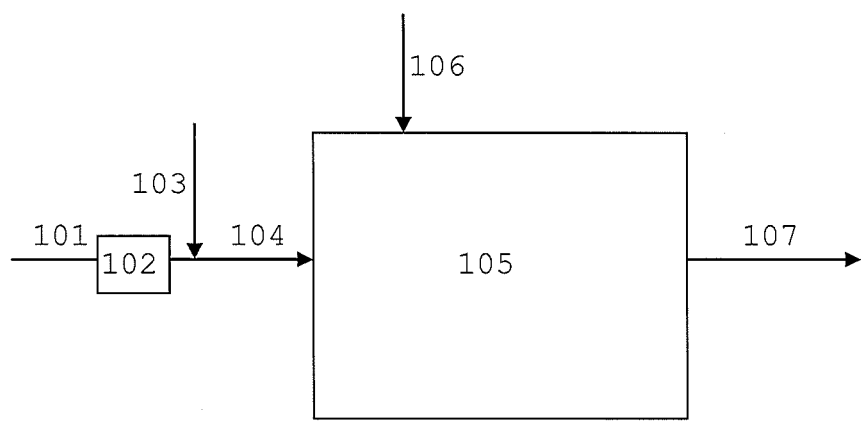

PROCESS FOR THE CONVERSION OF SACCHARIDE-CONTAINING FEEDSTOCK

PRIORITY CLAIM

The present application is a National Stage § 371 application of PCT/EP2014/056536, filed Apr. 1, 2014, which claims priority from European Patent Application EP13162502.2 filed Apr. 5, 2013, each of which are hereby incorporated by reference in their entirety.

FIELD OF THE INVENTION

The present invention relates to a process for the catalytic conversion of a saccharide-containing feedstock.

BACKGROUND OF THE INVENTION

In recent years increased efforts have been focussed on reducing the reliance on fossil fuels as a primary resource for the provision of fuels and commodity chemicals. Carbohydrates and related 'biomass' are seen as key renewable resources in the efforts to provide new fuels and alternative routes to desirable chemicals.

In particular, certain carbohydrates can be reacted with hydrogen in the presence of a catalyst system to generate polyols and sugar alcohols. Such processes have been described in Angew. Chemie. Int. Ed. 2012, 51, 3249 and US 2011/313212 and may be used to provide ethylene glycol and 1,2-propylene glycol, which are valuable materials with a multitude of commercial applications, e.g. as heat transfer media, antifreeze, and precursors to polymers, such as PET. Ethylene and 1,2-propylene glycols are traditionally made on an industrial scale by hydrolysis of the corresponding alkylene oxides, which are the oxidation products of ethylene and propylene, produced from fossil fuels.

A major problem encountered in the catalytic conversion of saccharides by known methods is the degradation of the saccharides in reactor feed pipes at high temperatures. Such degradation can lead to fouling and blocking of the pipes. One way to limit this problem is to supply the feed in the pipes at a lower temperature than the degradation temperature of the saccharides. The feed is, therefore, also at a lower temperature than the material in the reactor. However, degradation, fouling and blocking will still occur at the point where the feed pipes enter the reactor, due to the inevitable increase in temperature at this point.

Fouling and blocking of the feed pipes lead to reactor shut-downs for cleaning and/or replacement of the feed pipes and connections. This translates to higher running costs and reduced productivity. It would, therefore, be highly desirable to provide a method to reduce saccharide degradation in reactor feed pipes.

SUMMARY OF THE INVENTION

Accordingly, the present invention provides a process for the catalytic conversion of a saccharide-containing feedstock in a reactor, wherein saccharide-containing feedstock is provided to the reactor as a feed stream through a feed pipe and is contacted with a catalyst system in the reactor and a reaction product is continuously removed from the reactor and wherein the saccharide-containing feedstock is provided through the feed pipe as a pulsed flow and is alternated with a second feed stream comprising a solvent being provided through the same feed pipe.

BRIEF DESCRIPTION OF THE DRAWINGS

FIG. 1 is a schematic diagram of an exemplary, but non-limiting, embodiment of the process for the catalytic conversion of carbohydrates described herein.

DETAILED DESCRIPTION OF THE INVENTION

The present inventors have surprisingly found that saccharide degradation in feed pipes and at the point of entry to a reactor can be significantly decreased by the provision of the saccharide-containing feedstock as a pulsed flow alternating with a feed stream comprising a solvent.

By pulsed flow it is meant that the flow of the saccharide-containing feedstock is not continuous. The flow of the saccharide-containing feedstock will be turned on and off periodically over the course of the process.

When the flow of the saccharide-containing feedstock is turned on, the saccharide-containing feedstock is fed to the reactor as a continuous flow. In one embodiment of the present invention, a separate solvent feed may be added to the saccharide-containing feedstock or directly to the reactor while the flow of the saccharide-containing feedstock is turned on.

When the flow of the saccharide-containing feedstock is turned off, the amount of saccharide entering the reactor is reduced by at least 90%, preferably by at least 95%, more preferably by at least 98%, even more preferably by at least 99%, most preferably by essentially 100%, compared to when the flow of the saccharide-containing feedstock is turned on.

When the flow of the saccharide-containing feedstock is turned off, a second feed stream comprising a solvent is fed to the reactor through the feed pipe through which the saccharide-containing feedstock is fed to the reactor.

By reducing the amount of time that the saccharide feedstock is being fed to the reactor in substantial quantities and is passing through the pipes, the amount of degradation, fouling and blockages will be greatly reduced. This also allows the temperature in the feed pipe to be above the degradation temperature of the saccharide contained therein as the saccharide-containing feedstock will be at such a temperature for a limited period of time. Further, the second feed stream may be used to adjust the concentration of the saccharide in the reactor. The solvent may also rinse any residual saccharide and/or fouling out of the pipe and further aid in the prevention of blockages.

The second feed stream comprises a solvent. Suitably, at least 90 wt % of the second feed stream is a solvent. Preferably, at least 90 wt %, more preferably at least 95 wt %, even more preferably at least 98 wt %, most preferably substantially 100 wt % of the second feed stream is a solvent. However, in one embodiment of the invention, it is envisaged that a caustic material is added to the second feed stream. Such an embodiment has the advantage that the second feed stream may then actually remove any fouling in place in the feed pipe. In a further embodiment of the invention the pH in the reactor may be controlled by the addition of a pH buffer in the second feed stream.

The solvent in the second feed stream may be water, a $C_1$ to $C_6$ alcohol, or mixtures thereof. Preferably, the solvent is water.

The flow of the saccharide-containing feedstock will be turned on and off periodically over the course of the process. It is preferred that the time elapsed between turning the flow on each time and the time elapsed between turning the flow off each time are each maintained as a substantially regular time period. That is, the flow of the saccharide-containing feedstock is turned on for a first specific time period and then off for a second specific time period and then this is repeated throughout the process for substantially the same specific time periods. It is preferred that each of the first and second specific time are varied by not more than 10% of their lengths, more preferably not more than 5% of their lengths, even more preferably not more than 2% of their lengths, throughout the process. However, it is also envisaged that, throughout the process, after a number of repetitions, the process may be altered to function at different specific time periods.

Suitably, the ratio of the time that the flow of saccharide-containing feedstock is turned off to the time that the flow of saccharide-containing feedstock is turned on is at least 0.5:1, preferably at least 1:1, more preferably at least 2:1, even more preferably at least 4:1, most preferably at least 5:1. Suitably, the ratio of the time that the flow of saccharide-containing feedstock is turned off to the time that the flow of saccharide-containing feedstock is turned on is at most 20:1, preferably at most 10:1.

The second feed stream may be turned off when the flow of saccharide-containing feedstock is turned on, it may be reduced or it may remain flowing at the same rate for the entire process. Preferably, the second feed stream is turned off when the flow of saccharide-containing feedstock is turned on and is turned on for at least a portion of the time in which the flow of saccharide-containing feedstock is turned off. Suitably, at least a portion of the time in which the flow of saccharide-containing feedstock is turned off comprises at least 50%, more preferably at least 70%, even more preferably at least 90%, even more preferably at least 95 wt %, most preferably at least 99% of the time in which the flow of saccharide-containing feedstock is turned off.

The process requires a saccharide-containing feedstock. Said feedstock suitably comprises at least 1 wt % saccharide in a solvent. Preferably the saccharide-containing feedstock comprises at least 2 wt %, more preferably at least 5 wt %, even more preferably at least 10 wt %, most preferably at least 20 wt % saccharide in a solvent. Suitably, the saccharide-containing feedstock contains no more than 50 wt %, preferably no more than 40 wt % saccharide in a solvent.

It is envisaged that the composition and amount of the saccharide-containing feedstock and the amount of the second feed stream added to the reactor will be coordinated such that the concentration of saccharide in the solvent in the reactor while the reaction is proceeding is at least 0.01 wt % saccharide in solvent. Preferably the concentration of saccharide in solvent in the reactor is at least 0.02 wt %. Most preferably the concentration of saccharide in solvent in the reactor is at least 0.25 wt %. It is envisaged that the composition and amount of the saccharide-containing feedstock and the amount of the second feed stream added to the reactor will be coordinated such that the concentration of saccharide in the solvent in the reactor while the reaction is proceeding is at most 5 wt % saccharide in solvent. Preferably the concentration of saccharide in solvent in the reactor is at most 2 wt %. Most preferably the concentration of saccharide in solvent in the reactor is at most 1.5 wt %.

The saccharide-containing feedstock comprises at least one saccharide selected from the group consisting of mono-saccharides, disaccharides, oligosaccharides and polysaccharides. Examples of polysaccharides include cellulose, hemicelluloses, starch, glycogen, chitin and mixtures thereof. If the saccharide-containing feedstock comprises oligosaccharides or polysaccharides, it is preferable that it is subjected to pre-treatment before being fed to the reactor in a form that can be converted to glycols when contacted with hydrogen in the reactor in the presence of a suitable catalyst system. Suitable pre-treatment methods are known in the art and one or more may be selected from the group including, but not limited to, sizing, drying, grinding, hot water treatment, steam treatment, hydrolysis, pyrolysis, thermal treatment, chemical treatment, biological treatment.

Preferably, the saccharide-containing feedstock that is fed to the reactor, after pre-treatment if necessary, comprises one or more saccharide selected from the group consisting of glucose, sucrose and starch. Said saccharide is suitably present as a solution, a suspension or a slurry in the solvent.

The solvent may be water, a $C_1$ to $C_6$ alcohol, or mixtures thereof. Preferably, the solvent is water. As well as the solvent provided in the saccharide-containing feedstock there may also be further solvent already present in the reactor and/or added to the saccharide-containing feedstock as set out above. Said solvent is also suitably water, a $C_1$ to $C_6$ alcohol, or mixtures thereof. Preferably, all solvents are the same. More preferably, all solvents comprise water. Most preferably, all solvents are water.

Any reactor type suitable for a continuous flow process in which reaction product is continuously removed from the reactor may be used for the process of the present invention. For example, suitable reactor systems include ebullated catalyst bed reactor systems, immobilized catalyst reactor systems having catalyst channels, augured reactor systems, fluidized bed reactor systems, mechanically mixed reactor systems and slurry reactor systems, also known as a three phase bubble column reactor systems, and combinations thereof.

The temperature in the reactor is suitably at least 130° C., preferably at least 150° C., more preferably at least 170° C., most preferably at least 190° C. The temperature in the reactor is suitably at most 300° C., preferably at most 280° C., more preferably at most 270° C., even more preferably at most 250° C. Preferably, the temperature in the reactor is above the degradation temperature of the one or more saccharides in the saccharide feedstock. Preferably, the reactor is heated to a temperature within these limits before addition of any starting material and is maintained at such a temperature until all reaction is complete.

To further reduce degradation of the saccharide-containing feedstock, the temperature of the saccharide-containing feedstock is suitably maintained below the degradation temperature of the saccharides contained therein. However, as indicated previously, in one embodiment of the present invention the temperature in the feed pipe may advantageously be maintained above the degradation temperature of the saccharides contained therein as, in the process of the present invention, the saccharide-containing feedstock will be in the feed pipe for a much reduced amount of time. As used herein, the term degradation temperature relates to the temperature at which 1% of the saccharide present is degraded within an hour and will vary depending on the saccharides present.

Preferably, in order to maintain the temperature within the reactor, the temperature of the saccharide-containing feedstock is within 15° C. of the temperature of the reactor, more preferably within 10° C. of the temperature in the reactor, most preferably within 5° C. of the temperature in the reactor.

The temperature of the solvent stream may suitably be anywhere in the range of from ambient temperature to less than the boiling point of the solvent stream under the conditions of the process. In order to maintain the temperature within the reactor, it is preferred that the temperature of the solvent stream is within the range of from 10° C. below to 100° C. above the temperature of the reactor.

The pressure in the reactor is suitably at least 1 MPa, preferably at least 2 MPa, more preferably at least 3 MPa. The pressure in the reactor is suitably at most 16 MPa, preferably at most 12 MPa, more preferably at most 10 MPa, even more preferably at most 8 MPa, most preferably at most 6 MPa. Preferably, the reactor is pressurised to a pressure within these limits by addition of hydrogen before addition of any saccharide-containing feedstock. The pressure of hydrogen is maintained by addition of hydrogen as a separate feed stream throughout the process.

Preferably, the process of the present invention takes place in the presence of hydrogen. Preferably, the process of the present reaction takes place in the absence of air or oxygen. In order to achieve this, it is preferable that the atmosphere in the reactor be evacuated and replaced with hydrogen repeatedly, after loading of any initial reactor contents, before the reaction starts.

In one embodiment of the invention, the catalytic conversion of a saccharide-containing feedstock in a reactor comprises the conversion of one or more saccharides in the presence of hydrogen and a catalyst system to ethylene glycol and 1,2-propylene glycol. In this embodiment of the invention, the catalyst system used preferably comprises at least two active catalytic components comprising, as a first active catalyst component, one or more materials selected from transition metals from groups 8, 9 or 10 or compounds thereof, with catalytic hydrogenation capabilities; and, as a second active catalyst component, one or more materials selected from tungsten, molybdenum and compounds and complexes thereof.

Preferably, the first active catalyst component consists of one or more of the group selected from iron, cobalt, nickel, ruthenium, rhodium, palladium, iridium and platinum. This component may be present in the elemental form or as a compound. It is also suitable that this component is present in chemical combination with one or more other ingredients in the catalyst system. It is required that the first active catalyst component has catalytic hydrogenation capabilities and it is capable of catalysing the hydrogenation of material present in the reactor.

Preferably, the second active catalyst component comprises of one or more compound, complex or elemental material comprising tungsten, molybdenum, vanadium, niobium, chromium, titanium or zirconium. More preferably the second active catalyst component comprises one or more material selected from the list consisting of tungstic acid, molybedic acid, ammonium tungstate, ammonium metatungstate, ammonium paratungstate, tungstate compounds comprising at least one Group I or II element, metatungstate compounds comprising at least one Group I or II element, paratungstate compounds comprising at least one Group I or II element, heteropoly compounds of tungsten, heteropoly compounds of molybdenum, tungsten oxides, molybdenum oxides, vanadium oxides, metavanadates, chromium oxides, chromium sulfate, titanium ethoxide, zirconium acetate, zirconium carbonate, zirconium hydroxide, niobium oxides, niobium ethoxide, and combinations thereof. The metal component is in a form other than a carbide, nitride, or phosphide. Preferably, the second active catalyst component comprises one or more compound, complex or elemental material selected from those containing tungsten or molybdenum.

The catalyst components may be heterogeneous or homogeneous with respect to the solvent or solvents present in the reactor during the process of the present invention. The catalyst components may be preloaded into the reactor or, if they are in liquid form or present as a solution or slurry in a solvent, they may be fed into the reactor as required in a continuous or discontinuous manner during the process of the present invention.

Preferably, at least one of the active catalyst components is supported on a solid support. In this embodiment, any other active catalyst component may be present in either heterogeneous or homogeneous form. Said any other active catalyst component may also be supported on a solid support. In one embodiment, the first active catalyst component is supported on one solid support and the second active catalyst component is supported on a second solid support which may comprise the same or different material. In another embodiment, both active catalyst components are supported on one solid support.

The solid supports may be in the form of a powder or in the form of regular or irregular shapes such as spheres, extrudates, pills, pellets, tablets, monolithic structures. Alternatively, the solid supports may be present as surface coatings, for examples on the surfaces of tubes or heat exchangers. Suitable solid support materials are those known to the skilled person and include, but are not limited to aluminas, silicas, zirconium oxide, magnesium oxide, zinc oxide, titanium oxide, carbon, activated carbon, zeolites, clays, silica alumina and mixtures thereof.

Suitably, the weight ratio of the first active catalyst component to the second active catalyst component is in the range of from 0.02:1 to 3000:1, preferably in the range of from 0.1:1 to 100:1, on the basis of the weight of metal present in each component.

The weight ratio of the first active catalyst component (based on the amount of metal in said component) to sugar is suitably in the range of from 1:100 to 1:10000. The weight ratio of the second active catalyst component (based on the amount of metal in said component) to sugar is suitably in the range of from 1:10 to 1:1000.

An effluent stream comprising ethylene glycol and 1,2-propylene glycol is continuously removed from the reactor. Said effluent stream may also contain water, hydrogen, unreacted saccharide, intermediates, by-products and catalyst materials. Said catalyst materials may be the result of decomposition of the catalyst system in the reactor or may be catalyst material present as part of an at least partially homogeneous catalyst system. Such catalyst materials will need to be separated from the effluent stream and optionally recycled to the reactor or a reactor feed stream.

The remaining effluent stream will then require separation and purification of the desired products. Unreacted saccharides and intermediates may be separated and recycled to the saccharide-containing feedstock. Hydrogen and water may also be separated and recycled to reactor feed streams.

An embodiment of the present invention will now be described by way of example only and with reference to the accompanying non-limiting FIGURE.

The flow of saccharide-containing feedstock 101 is controlled by means of device 102, which may be a switch or a valve or the like, to provide a pulsed flow through reactor inlet pipe 104 into reactor 105. A further feed stream comprising solvent is provided through pipe 103 for at least part of the time when the flow of the saccharide-containing feedstock is turned off.

What is claimed is:

1. A process for the catalytic conversion of a saccharide-containing feedstock, in the presence of hydrogen and a catalyst system, to ethylene glycol and 1,2-propylene glycol in a reactor at a temperature in the range of from 150 to 250° C., wherein saccharide-containing feedstock is provided to the reactor as a feed stream through a feed pipe and is contacted with the catalyst system in the reactor and a reaction product is continuously removed from the reactor and wherein the saccharide-containing feedstock is provided through the feed pipe as a pulsed flow and is alternated with a second feed stream comprising a solvent being provided through the same feed pipe.

2. The process according to claim 1, wherein the flow of the saccharide containing feedstock is turned on and off such that when the flow of the saccharide containing feedstock is turned off, the amount of saccharide entering the reactor is reduced by at least 90% when compared with when the flow of the saccharide containing feedstock is turned on.

3. The process according to claim 1, wherein the second feed stream is provided to the reactor for at least 90% of the time in which the flow of the saccharide containing feedstock is turned off.

4. The process according to claim 1, wherein the ratio of the time in which the flow of the saccharide containing feedstock is turned on to the time in which the flow of the saccharide containing feedstock is turned off is in the range of from 0.5:1 to 20:1.

5. The process according to claim 1, wherein the catalyst system comprises at least two active catalytic components comprising, as a first active catalyst component, one or more materials selected from transition metals from groups 8, 9 or 10 or compounds thereof, with catalytic hydrogenation capabilities; and, as a second active catalyst component, one or more materials selected from tungsten, molybdenum and or compounds or complexes thereof.

6. The process according to claim 1, wherein the solvent comprises water.

7. The process according to claim 1, wherein the saccharide-containing feedstock comprises one or more of glucose, sucrose and starch.

8. The process according to claim 1, wherein pressure in the reactor is in the range of from 1 to 16 MPa.

9. The process according to claim 1, wherein the second feed stream remains flowing at the same or a reduced rate for the entire process.

10. The process according to claim 1, wherein the temperature of the saccharide-containing feedstock is within 15° C. of the temperature of the reactor.

11. The process according to claim 1, wherein the temperature of the second feed stream comprising the solvent is within the range of from 10° C. below to 100° C. above the temperature of the reactor.

* * * * *